(12) United States Patent
Gutierrez Martinez

(10) Patent No.: US 10,041,918 B2
(45) Date of Patent: Aug. 7, 2018

(54) ELECTRONIC NOSE AND TONGUE DEVICE FOR REAL-TIME MONITORING AND ANALYSIS OF LIQUID AND GASEOUS SUBSTANCES

(71) Applicant: NUXTU S.A.S, Bogota (CO)

(72) Inventor: Felipe Eduardo Gutierrez Martinez, Bogota (CO)

(73) Assignee: NUXTU S.A.S., Bogota (CO)

( * ) Notice: Subject to any disclaimer, the term of this patent is extended or adjusted under 35 U.S.C. 154(b) by 0 days.

(21) Appl. No.: 15/348,117

(22) Filed: Nov. 10, 2016

(65) Prior Publication Data
US 2017/0131253 A1    May 11, 2017

(30) Foreign Application Priority Data
Nov. 10, 2015   (CO) .................................. 15 268355

(51) Int. Cl.
*G01N 27/416*    (2006.01)
*G01N 27/403*    (2006.01)
(Continued)

(52) U.S. Cl.
CPC ......... *G01N 33/0034* (2013.01); *C02F 1/008* (2013.01); *G01N 27/04* (2013.01); *G01N 27/403* (2013.01); *G01N 27/48* (2013.01); *G01N 33/0009* (2013.01); *G01N 33/0022* (2013.01); *G01N 33/0032* (2013.01);
(Continued)

(58) Field of Classification Search
CPC ............... G01N 27/407; G01N 27/403; G01N 27/4141; G01N 27/02; G01N 27/04; G01N 33/0009; G01N 33/0022; G01N 33/0031

See application file for complete search history.

(56) References Cited

U.S. PATENT DOCUMENTS

| | | | |
|---|---|---|---|
| 6,422,061 B1* | 7/2002 | Sunshine ............. | G01N 29/022 340/603 |
| 2014/0240120 A1* | 8/2014 | Mao ..................... | G08B 27/008 340/539.11 |

OTHER PUBLICATIONS

A. Talaie, J.Y. Lee, H. Eisazadeh, K. Adachi, J.A. Romagnoli and T. Taguchi, "Towards a Conducting Polymer-based Electronic Nose and Electronic Tongue" Iranian Polymer Journal / vol. 9, Nov. 1, 2000, pp. 3-10.

(Continued)

*Primary Examiner* — Alexander S Noguerola
(74) *Attorney, Agent, or Firm* — Hackler Daghighian Martino & Novak

(57) ABSTRACT

The present invention relates to an electronic, integrated, nose and tongue device, which can be stationary or portable (movable) and is designed for real-time monitoring and analyzing information about liquid substances of any kind, as well as toxic, flammable, choking, radioactive and/or polluting gases present in the air or water, which is achieved by the use of artificial intelligence algorithms capable of classifying and training the system so as to recognize the different sign patterns sent by the electronic nose and the electronic tongue. Embodiments described herein can be used in outdoor conditions and complicated areas or connected to water treatment systems, such as those used in electro-coagulation, wherein such a device may be connected to the inlet piping of the treatment systems and can determine how much energy must be used by the electro-coagulators according to the contamination degree of the water.

13 Claims, 29 Drawing Sheets

(51) Int. Cl.
*G01N 33/00* (2006.01)
*G01N 33/18* (2006.01)
*G01N 27/48* (2006.01)
*C02F 1/00* (2006.01)
*G01N 27/04* (2006.01)

(52) U.S. Cl.
CPC ......... *G01N 33/0073* (2013.01); *G01N 33/18* (2013.01); *G01N 2033/0093* (2013.01)

(56) References Cited

OTHER PUBLICATIONS

Jehuda Yinon, "Detection of Explosives by Electronic Noses", University of Central Florida, Analytical Chemistry, Mar. 1, 2003, pp. 99A-105A.

Grace Industries, Inc. "Electronic Nose" Technical Paper Jan. 1, 1982. Available at "https://ntrs.nasa.gov/search.jsp?R=20030002836".

Diego L. Garcia-Gonzalez and Ramon Aparicio, "Sensors: From Biosensors to the Electronic Nose" Grasas y Aceites, vol. 53, Fasc. 1, 2002, pp. 96-114.

\* cited by examiner

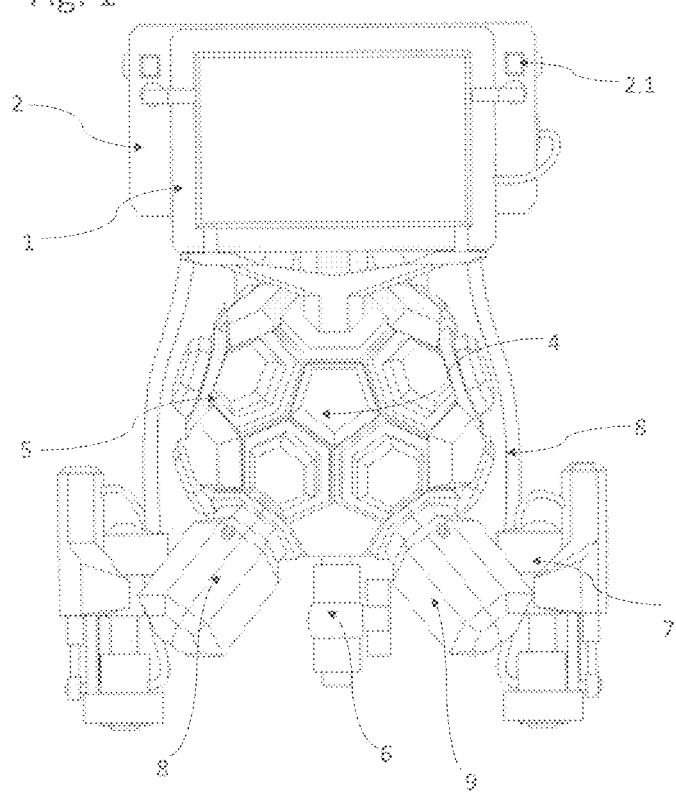

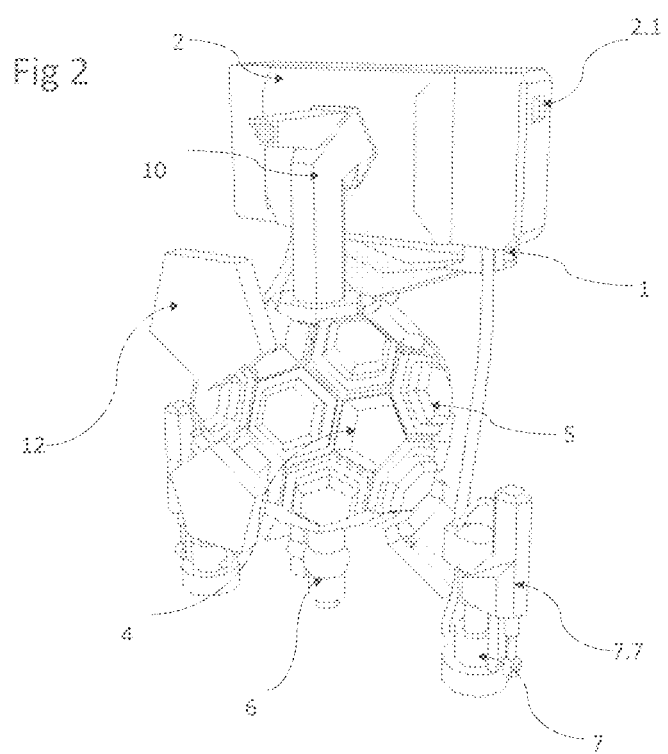

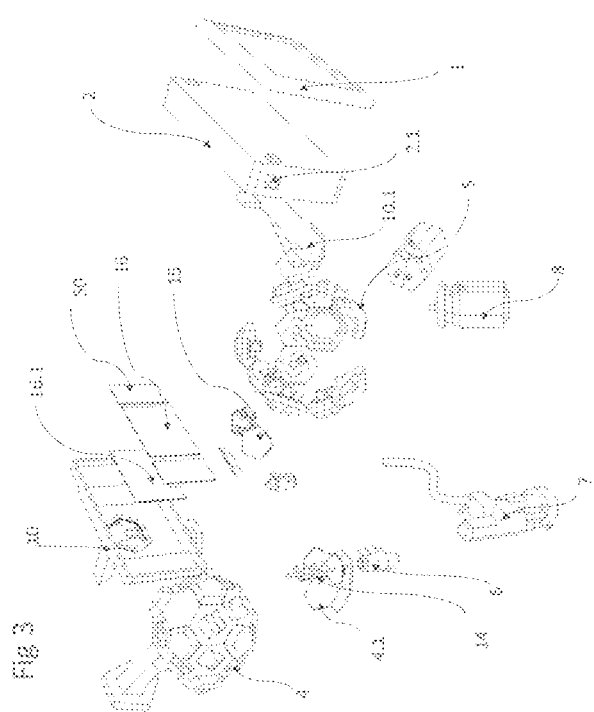

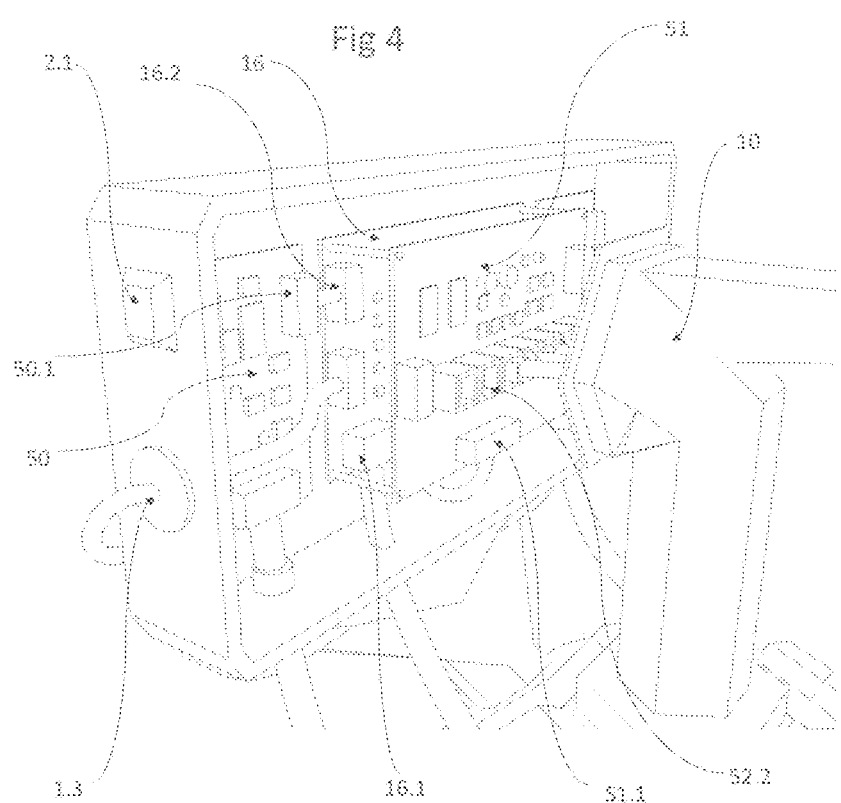

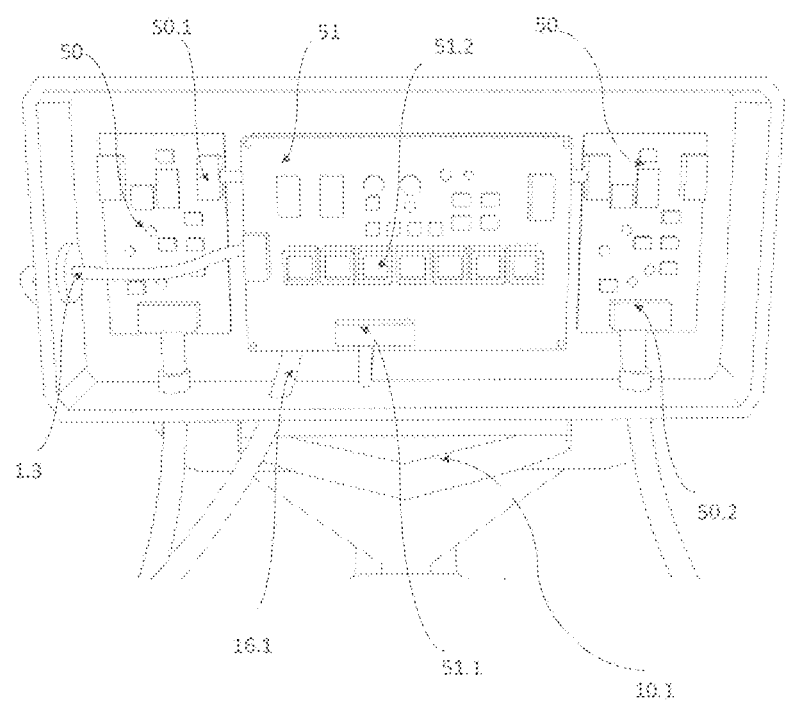

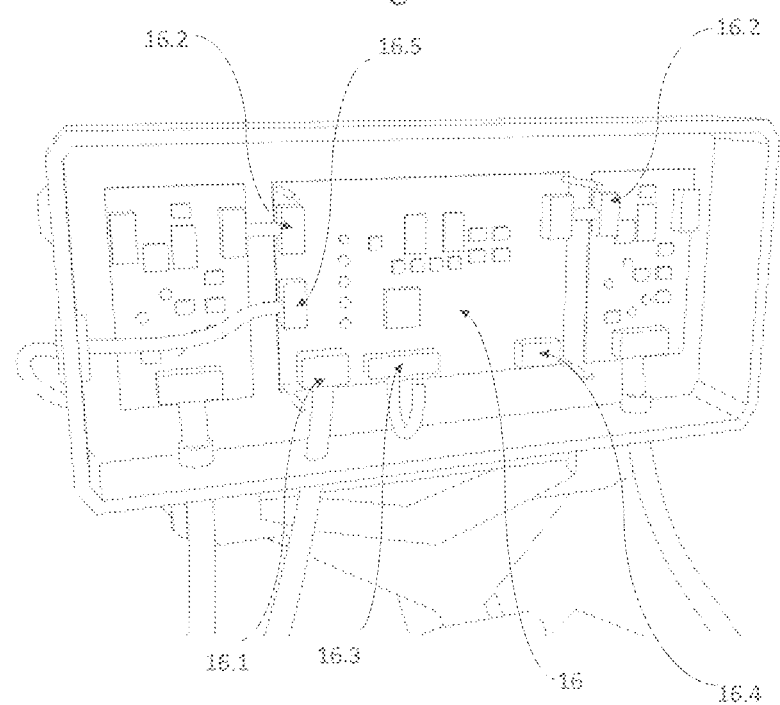

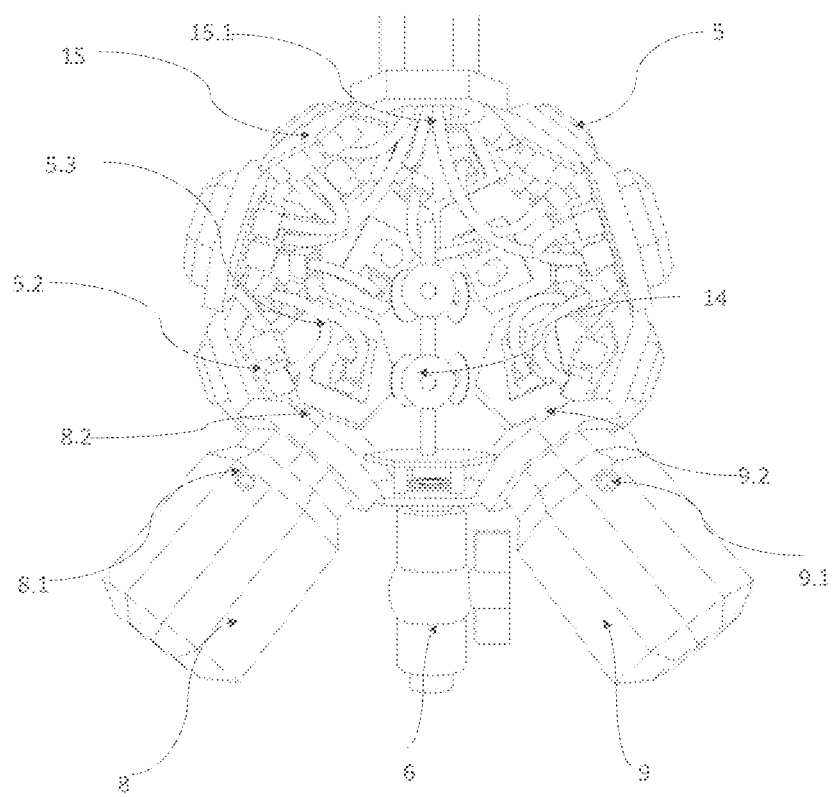

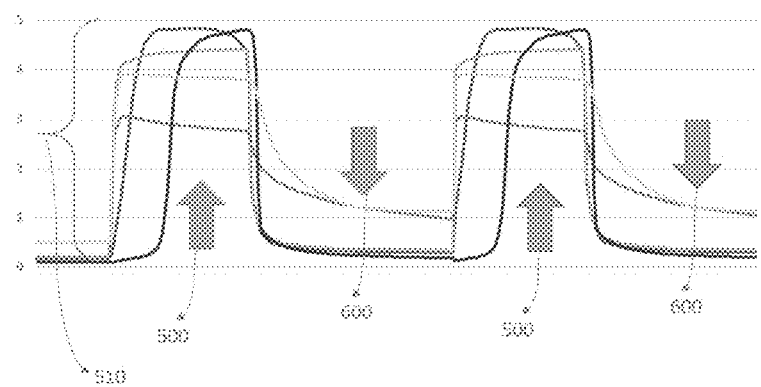

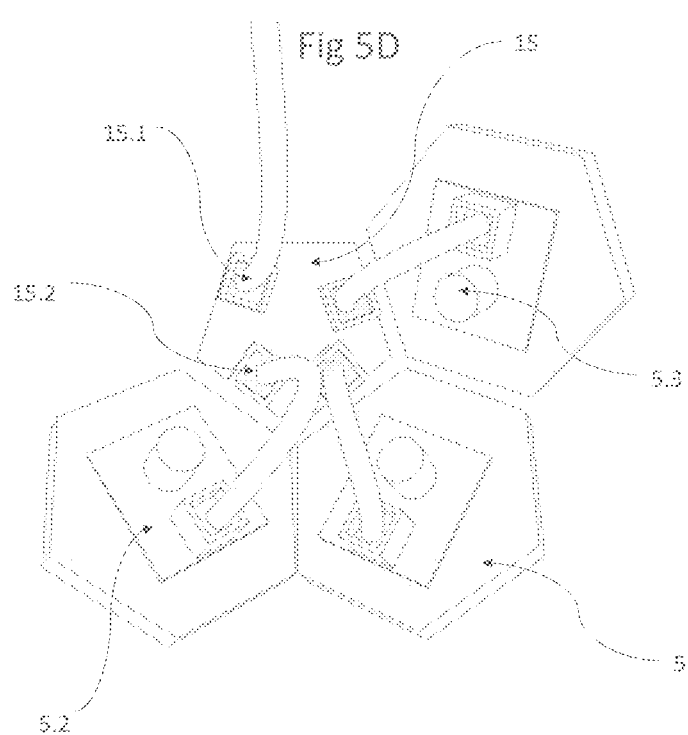

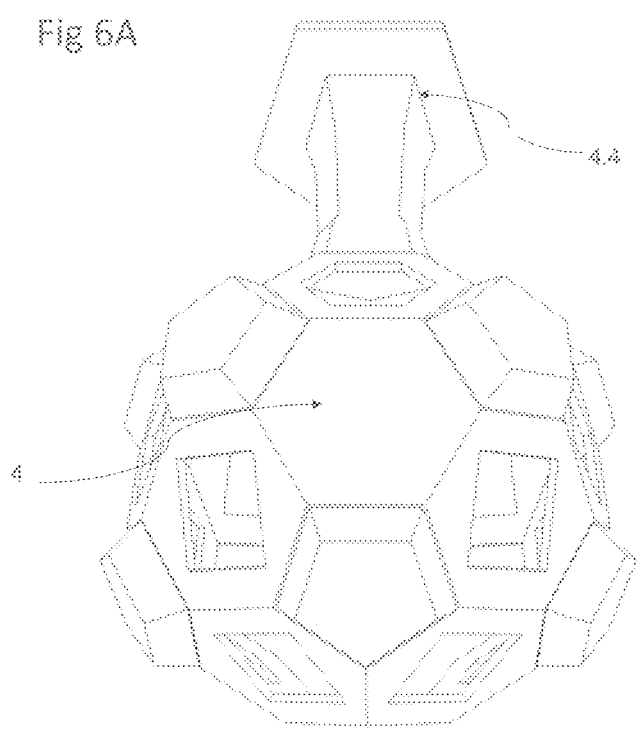

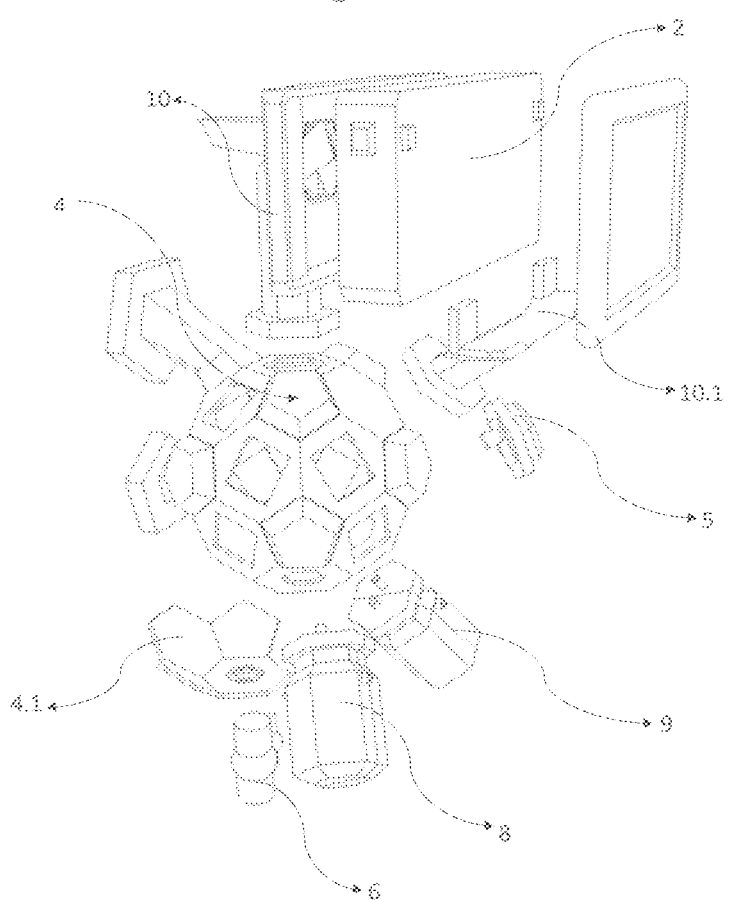

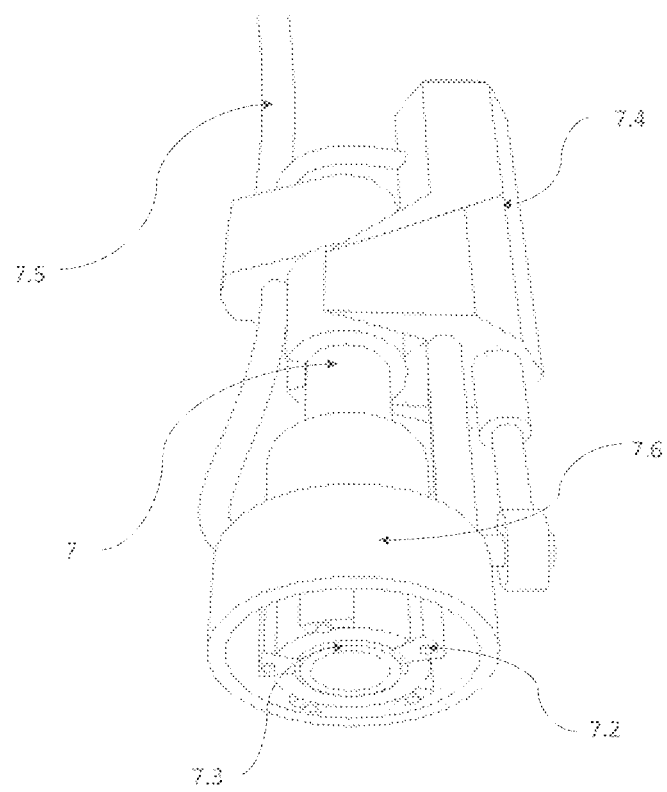

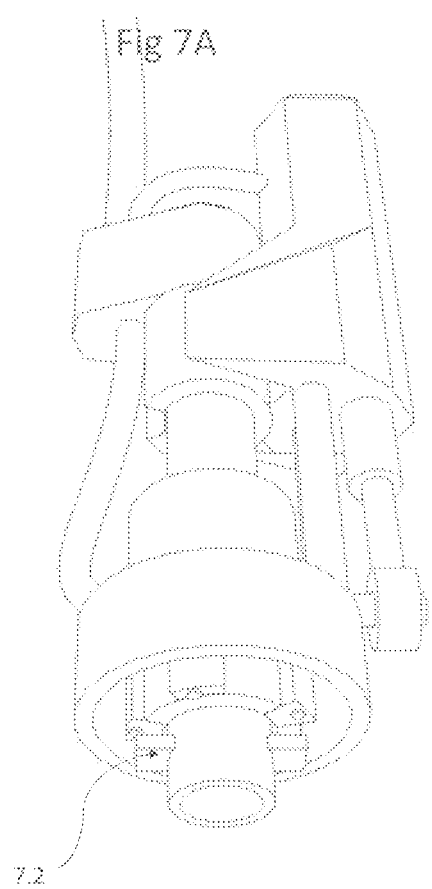

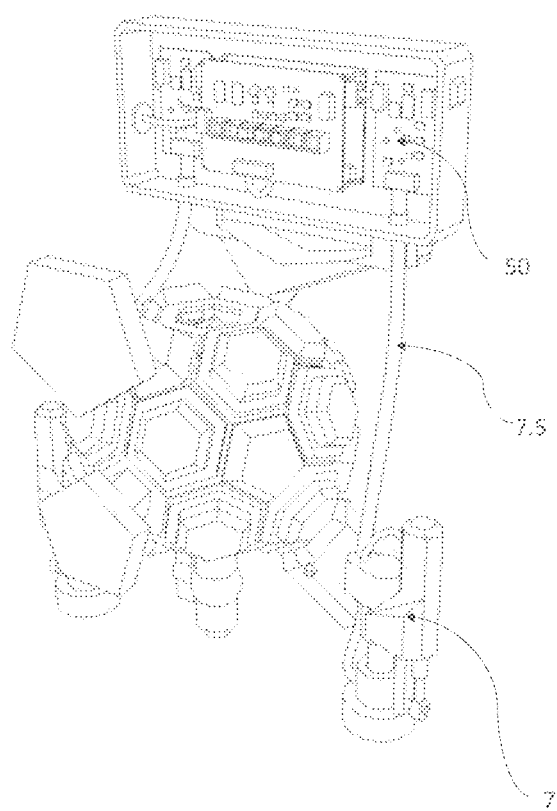

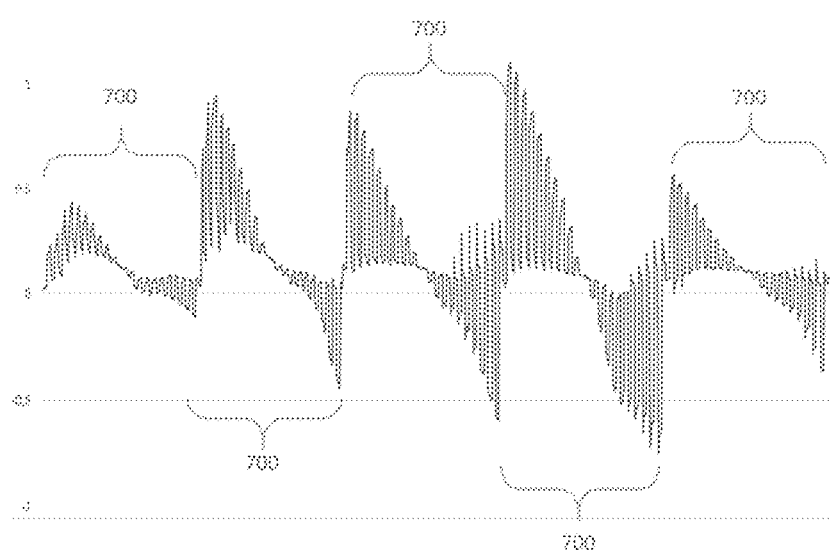

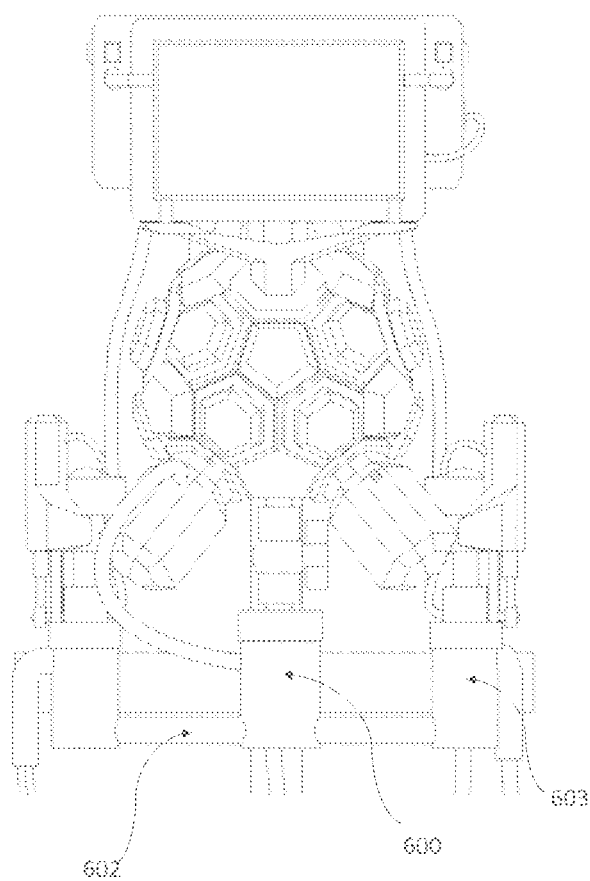

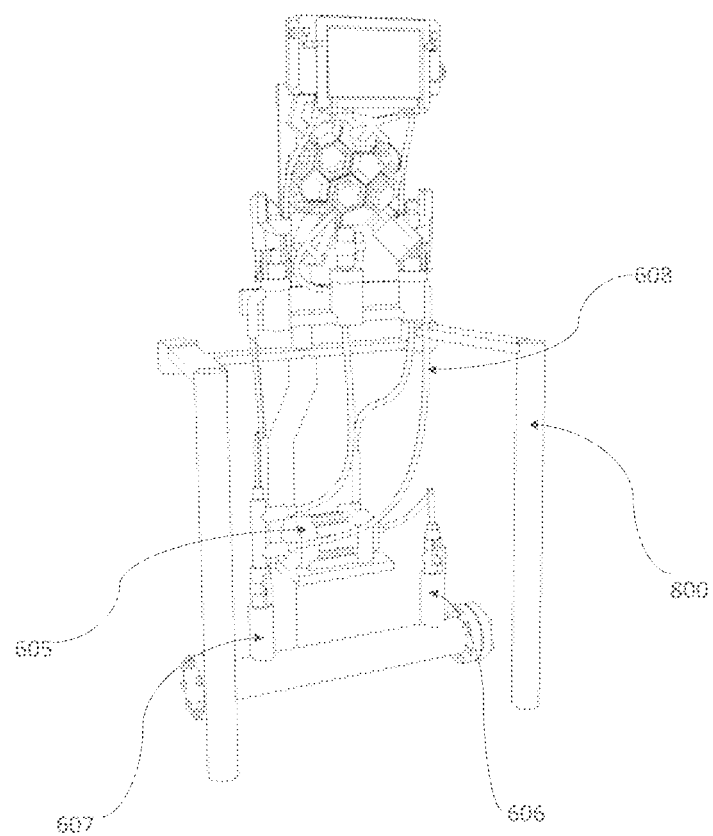

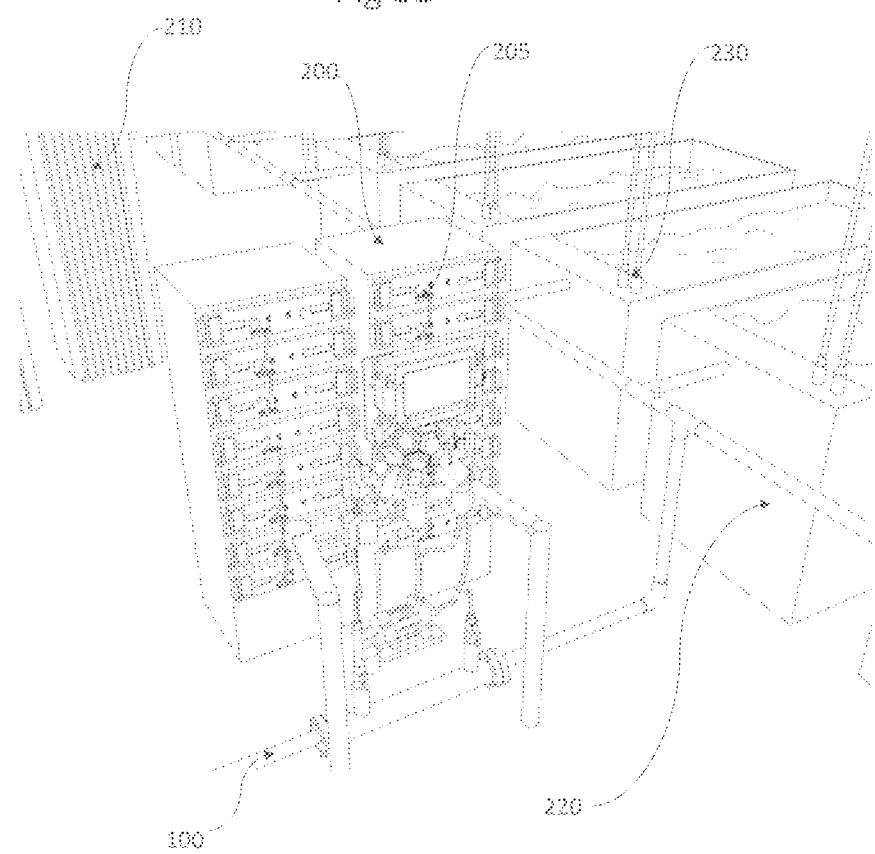

ELECTRONIC NOSE AND TONGUE DEVICE FOR REAL-TIME MONITORING AND ANALYSIS OF LIQUID AND GASEOUS SUBSTANCES

CROSS-REFERENCE TO RELATED APPLICATION

This application is a continuation-in-part of Colombian Application No. 15-268355, filed Nov. 10, 2015 which is incorporated herein in its entirety by reference.

TECHNICAL FIELD

The present invention relates to an electronic, integrated, nose and tongue device, which can be stationary or portable and is designed for real-time monitoring and analyzing liquid substances.

BACKGROUND OF THE INVENTION

Nowadays, technologies for the analysis and monitoring of fluids and/or gases existent in the state of the art are very limited in their use, given they can only detect six gases in real time, but in some areas it is necessary to monitor more than fifty gases in real time, such as in the case of the oil industry, which leads to conclude that this technology does not currently exist.

What is more, nowadays it is also important to have devices able to monitor both in the environment as in the water, that can detect hazardous substances in the water for consumers and also for the ecosystem present in the water. The environmental aspect is of great importance and must abide by a series of regulations that define the amount of liquids that can be polluted and its subsequent processing to avoid any inconvenient or affecting the ecosystem.

Thus, a plurality of divulgations exists related with apparatus or devices used to analyze and monitor both liquid and gaseous substances, where we can find the RU 2533692 document that shows a device that combines analytical instruments for electronic nose and electronic tongue, where these elements are set as an acoustic multiplexor arrangement that includes a flat parallel plaque made of piezoelectric crystal, with its crystallographic axis that rests on the plain of the plaque and that passes through the center of the conditional plaque; Interdigital Transducers located symmetrically in pairs on the working side of the plaque and that form the acoustic channel system, where the propagation directions of the acoustic wave intersect in the center of the conditional plaque, where it has a circular zone for the location of a sample.

However, the device described in this document has the disadvantage of being limited to acoustic signals and its properties, which is why it is not suitable for use in the simultaneous analysis and monitoring of both liquid and gaseous substances.

Furthermore, we can also find the document MX 2014010070 that discloses an electronic tongue or nose sensor for the analysis of a sample or for the detection of an objective, that in its surface includes a sensor which has a plurality of sensitive areas that include each one at least one receptor, where each sensible zone emits a signal that can be measured and that is generated by the interaction of at least one constituent of the sample or an objective with at least one receptor. Thus, the sensor includes at least three sensitive areas that differ from one another in terms of their respective compositions of receiver, where at least one of the sensitive areas comprises a mixture of at least two different receptors, while the other two sensitive areas include each at least two receivers.

However, the prior device has as a disadvantage being restrictive to the analysis and measurement of the substances to a liquid or a gas, meaning the sensor can be of electronic tongue or of electronic nose, fact that limits its field of application and is unwanted, because the sensors must be specific and cannot make multiple measurements at the same time.

Finally, we have the document GB 909415 that relates to a method and an apparatus for the analysis of fluids, where a liquid is continuously tested for the analysis in relation to a substance that can evolve from liquid to gaseous form or that can turn into gas, through the introduction of a stream of a reagent in a current of the liquid, by passing the resulting current through a gas/liquid separator and treating at least a part of the gas stream separated for analysis. The device includes a liquid/gas separator connected to the duct Principle del formulario and the appliance for additional treatment connected to the gas outlet of the separator.

Principio Del Formulario

In accordance with the foregoing, it is clear to a person skilled in the field of the state of the art, that there is a need for designing and implementing a device that allows to carry out monitoring and analysis in real time, both in liquid substances like gas substances simultaneously, without the need for additional sensors or changing items to adapt the device for the application where its going to be used. Likewise, it is required for the device or appliance to have such a versatility so that it adapts to these two scenarios, in the monitoring of toxic, flammable and radioactive substances, that can be present in the atmosphere or in the water, allowing it to detect hundreds of substances in real time while having the versatility to connect to a water treatment plant determining the amount of energy needed, according to the level of pollution in the water, providing information that will result in great savings in maintenance and energy.

Furthermore, it is desirable that the device can be used in any industry and preferably, that it can be easily and comfortably transported by the user, so that measures and analysis can be carried out in remote zones and under any climatic conditions.

SUMMARY

The present invention relates to an electronic, integrated, nose and tongue device, which can be stationary or portable (movable) and is designed for real-time monitoring and analyzing information about liquid substances of any kind, as well as toxic, flammable, choking, radioactive and/or polluting gases present in the air or water, which is achieved by the use of artificial intelligence algorithms capable of classifying and training the system so as to recognize the different sign patterns sent by the electronic nose and the electronic tongue. The device of the present invention has a design which allows its use in a continuous manner and in outdoor conditions and complicated areas.

Similarly, the device of the present invention also can be connected to water treatment systems, such as those used in electro-coagulation, Ultraviolet radiation, ozone treatment, capacitive deionization or other types of treatment plants, wherein such device may be connected to the inlet piping of the treatment systems and can determine how much energy (voltage and amperage) is used according to the contamination degree of the water.

Likewise, the technology of the invention can be used in any industry where analysis and monitoring of any liquid or substance being vital in a production process is required, such as water treatment plants, juices, foods, liquors, perfumery, pharmacology, medicine and defense. It can also be used in working environments wherein there is a high probability of funding toxic, flammable, choking, radioactive and contaminant substances in the environment or in the water, wherein these substances are recurrent in works such as mining, oil refinery, conventional gas or oil extraction fields, oil piping, hydraulic fracking gas and oil extraction fields, processing and producing plants of chemicals, steel plants, waste and drinking water treatment plants.

To this end, a real-time, in-situ monitoring and analyzing device of liquid or gaseous substances is provided. In a preferred embodiment, the device comprises: an electronic nose module having an electrical board; one or more electronic tongue modules each having an electrical board; an electrical board box; a computer located in the board box; an alarm mechanism located the board box; a chassis having assembled thereto a plurality of sensing modules, concentrator boards, a valve, expulsion and suction pumps, and heaters; a main support assembled to the chassis and having inside thereof connection cables for the plurality of sensing modules the expulsion and suction pumps; and a programmable power source, wherein the nose module and tongue module are connected to a data processing and acquisition board which is directly connected to the computer; and wherein each of the nose module and tongue module are connected to sensors in the plurality of sensing modules.

In some embodiments, the electrical board box is armored, anti-explosions and water resistant. In some embodiments, the main chassis has a cover and a capsule or chamber is defined inside the chassis.

In yet other embodiments, the electronic nose module includes 10 to 40 sensors, including temperature, relative humidity, gamma radiation, beta, X ray, and 10 to 30 gas sensors.

Often, the suction pump comprises some suction orifices and a chassis where all the sensors are located. In some embodiments, the gas expulsion pump comprises an orifice located in the upper part of the pump and some expulsion orifices.

In some embodiments, the hub boards have a data transfer connector per each three sensors and it has a total of 6 to 10 hub boards connected to the sensors, wherein a hub board is connected to the resilient heaters, and wherein each hub board is connected to the nose board and is located in the chassis.

In certain embodiments, the chassis further comprises a computer fastener, and wherein said chassis can be installed in walls or fixed surfaces.

The electronic tongue module is composed by working electrodes connected to the electrode head, and a reference electrode. In preferred embodiments, the working electrodes are comprised of different materials, such as gold, platinum, silver, titanium, rhodium, iridium, or non-precious such as zinc, lead, copper, cobalt and graphite.

Some embodiments further comprise a support structure in which a suction pump and some sample containers are incorporated. Some embodiments, may also further comprise a remote-control connection module, such as modem connected to the computer.

Often, the device is portable. The device may also be connected to a water treatment system.

In yet other embodiments, a monitoring system is provided. In preferred embodiments, the monitoring system comprises: an electronic nose module comprising: a structural frame in the shape of geodesic dome with a plurality of openings on hexagonal faces of the geodesic dome; a plurality of modules mounted in the openings wherein each opening in the structural frame is filled to form an enclosed chamber on an interior of the structural frame; wherein at least one of the modules includes an intake port to allow gas to enter the enclosed chamber; wherein a plurality of the modules are sensor modules arranged to sense the gas in the interior of the enclosed chamber; wherein at least one module is an intake pump and at least one module is an output pump.

In preferred embodiments, the monitoring system further comprises at least one tongue sensor including a plurality of electrodes. The monitoring system may have a structural frame that is comprised of a plurality of hexagonal and pentagonal faces. In some of those embodiments, exactly twelve of the faces are pentagon shaped. In some embodiments, the openings are square shaped. In yet other embodiments, a plurality of the pentagonal faces are fixed hub boards.

A method for inputting parameters to define when a substance has been detected is also provided. In preferred embodiments, the method comprises: displaying a three-dimensional graph on a screen where each axis of the three-dimensional graph represents a particular parameter for detecting a substance; defining a rectangular volume in the three-dimensional graph; displaying the rectangular volume in the three-dimensional graph; using limits of the rectangular volume to establish parameters defining when a substance has been detected. analyzing a substance and displaying a point on the three-dimensional graph that represents the detected substance in terms of the axis of the three-dimensional graph; determining whether the point is within the rectangular volume.

In some of the embodiments of the method, the analyzing step is performed by a nose sensor and a tongue sensor and data from both sensors is analyzed by a single processor. In some embodiments, the displaying steps occur on a touch screen that allows the rotation of the three-dimensional graph.

In preferred embodiments, the rectangular volume is defined by entering a center point and widths for the rectangular volume in each axis of the three-dimensional graph.

A process for displaying the results from a monitoring system is also provided. In preferred embodiments, the process comprises: receiving input from a plurality of sensors in a nose module and displaying the results on a two-dimensional graph as continuous lines where the scale of the x-axis and the continuous lines are constantly updated to accommodate new input from the plurality of sensors; and, receiving input from a tongue module and simultaneously displaying the results in a two-dimensional graph as a continuous line where the scale of the x-axis and the continuous line are constantly updated to accommodate new input from the tongue module.

In those embodiments, the tongue module may be comprised of a plurality of electrodes where at least one electrode is a reference electrode. Preferably, both the tongue module and nose module are processed through a single processor using an artificial intelligence algorithm.

A process for detecting a contaminate with a nose sensor is also provided. In preferred embodiments, the process comprises: analyzing each of the sensor signals in a plurality of sensors for a signal to noise ratio; Selecting a subset of the plurality of sensors with the highest signal to noise ratio wherein the signal to noise ratio of the sensors is determined based on the response from the training samples.

BRIEF DESCRIPTION OF THE DRAWINGS

FIG. 1 corresponds to a general front view of the electronic nose and tongue device of the present invention.

FIG. 2 corresponds to a back perspective view of the device of FIG. 1.

FIG. 3 corresponds to a general exploded view of the device of the present invention, wherein all its components and/or parts are shown in detail.

FIG. 4 corresponds to a detailed view of the board box and its inner elements.

FIGS. 4A and 4B correspond to detailed views of the different boards which are inside the board box of FIG. 4.

FIG. 5 corresponds to a general view of the electronic nose part of the device of the present invention.

FIG. 5B corresponds to a graph showing the graphs generated by the sensors being part of the electronic nose.

FIG. 5D corresponds to a detailed view of the inner part of the electronic nose of FIG. 4 with the sensors, connectors and other internal elements.

FIG. 6A corresponds to a plan front view of the chassis of FIG. 6.

FIG. 6B corresponds to a general view of the way how the chassis of FIG. 4 is assembled with the other elements or modules of the device of the present invention.

FIG. 7 corresponds to a general view of the electronic tongue module of the device of the present invention.

FIG. 7A corresponds to a detailed view of the electronic tongue module of FIG. 7 with the electrodes in an outside position.

FIG. 7B corresponds to a general view of the electronic tongue module in the device of the present invention.

FIG. 7C corresponds to a graph showing the graphs generated by the signals from the working electrodes in a substance analyzed in the electronic nose.

FIG. 8 corresponds to a front view of the way how the electronic nose and tongue modules are assembled.

FIG. 8A corresponds to a general view of the device of the present invention with the nose and tongue modules being duly coupled and assembled.

FIG. 8B corresponds to a general perspective view of the device with the modules in functioning.

DETAILED DESCRIPTION OF THE INVENTION

Figure 5A:
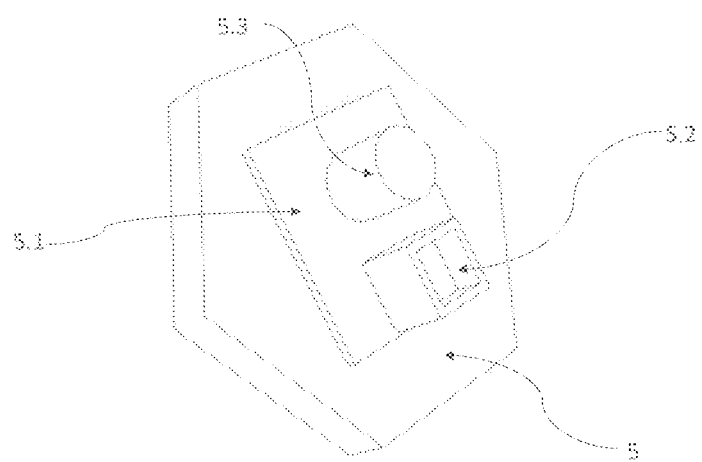
FIG. 5A corresponds to a detailed view of one of the sensors composing the electronic nose of FIG. 4.
Figure 5C:
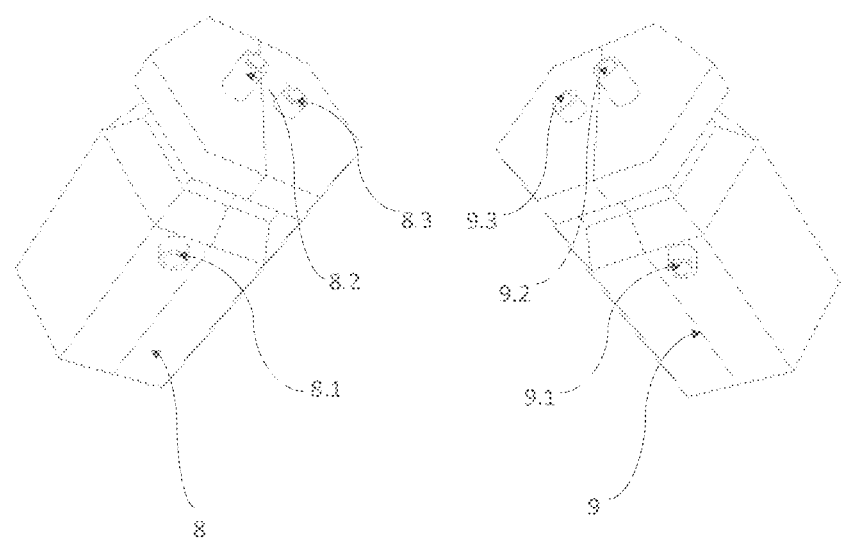
FIG. 5C corresponds to a detailed view of the suction and gas expulsion pump of the electronic nose of FIG. 4.

The following detailed description includes representative examples utilizing numerous features and teachings, both separately and in combination, and describes numerous embodiments in further detail with reference to the attached drawings. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense, and are instead taught merely to describe particularly representative examples of the present teachings.

Some portions of the detailed descriptions that follow are presented in terms of algorithms and sequences of operations which are performed within a computer memory. These algorithmic descriptions and representations are the means used by those skilled in the data processing arts to most effectively convey the substance of their work to others skilled in the art. An algorithm or sequence of operations is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing," "computing," "calculating," "determining," "displaying" or the like, refer to the action and processes of a computer system, or similar electronic device, that manipulates and transforms data represented as physical (electronic) quantities within the computer system's registers and memories into other data similarly represented as physical quantities within the electronic device's memory or registers or other such information storage, transmission or display devices.

The embodiments disclosed also relate to an apparatus for performing the operations herein. This apparatus may be specially constructed for the required purposes, or it may comprise a general purpose processor selectively activated or reconfigured by a computer program stored in the electronic device. Such a computer program may be stored in a computer readable storage medium, such as, but is not limited to, any type of disk, including floppy disks, optical disks, CD-ROMs, and magnetic-optical disks, read-only memories (ROMs), random access memories (RAMs), EPROMs, EEPROMs, Flash memory, magnetic or optical cards, or any type of media suitable for storing electronic instructions, and each coupled to a computer system bus.

The algorithms presented herein are not inherently related to any particular electronic device or other apparatus. Various general purpose systems may be used with programs in accordance with the teachings herein, or it may prove convenient to construct a more specialized apparatus to perform the required method steps. The required structure for a variety of these systems will appear from the description below. It will be appreciated that a variety of programming languages may be used to implement the teachings of the embodiments as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help understand how the present teachings are practiced, but not intended to limit the dimensions and the shapes shown in the examples.

The present invention defines a device for monitoring and analyzing in real time in-situ liquid and/or gaseous substances, which is based in electronic nose and tongue modules, which will be defined below in a preferred embodiment.

In this regard, FIGS. 1, 2 and 3 show the components of the Electronic Nose-Tongue device, comprising the board box 2, which is the element where the portable computer 1 is located, the box is armored and anti-explosions and water resistant, which allows the proper manipulation of the portable computer 1. The board box 2 has some characteristics which allow severe outdoor conditions to be handled. In the upper part of the board box 2 there are luminous devices 2.1 of high levels alert for dangerous substances, said luminous devices 2.1 provide a red light in case very high concentrations of dangerous substances are found which are sensed by the electronic nose or by the electronic tongue. The portable computer 1 is located in the front part of the board box 2, which is responsible of running specialized computer software for the analysis of the received data, wherein such software further allows the electronic nose-tongue device to be turned on and off and also performs the learning and identification of the information through the algorithm with the information received by the electronic nose-tongue device.

Similarly, the portable computer 1 is connected to the processing board 16, wherein such board 16 is responsible of the acquisition of data and the pre-processing of information, and is connected via an USB port 1.3 to the computer 1. Inside the main support 10, the cables for the nose and pumps sensors pass through, connecting thereby to the nose board 51. The main support 10 is assembled in the upper part of the chassis 4, while the sensing modules 5, the hub boards 15, the valve 6, the 2 pumps 8, 9 and the heaters 14 are assembled in the chassis 4. These heaters 14 are the responsible of balancing the internal temperature and humidity, which occurs due to the data sent by the temperature and the humidity sensors, and through an algorithm according to the temperature and the humidity, the temperature of the heaters is adjusted, wherein this procedure is very useful in countries with seasons, since slight changes in the temperature and humidity in the capsule significantly alter the signal of the gas sensors. The main chassis 4 further comprises a cover 4.1 which allows the internal assembly of the system.

Inside the chassis 4, a capsule or chamber is formed where all gases sent by the suction pump 9 are entered passing first through the valve 6, wherein such gases pass to be detected by a range of sensor composing the electronic nose, which will be formed by a plurality of sensors which detect different gases, H2S sensor, temperature sensor, humidity sensor and radiation detection sensor. Thus, the gases are inside the capsule or chamber the time determined by the user by previous configuration in the computer software in the computer 1. Then, the gases are expelled by the gas expulsion pump 8 so as to empty the capsule or chamber during the time configured by the user in the computer 1. Then, the cycle is repeated with the suction pump 9.

In a preferred embodiment of the invention, the electronic tongue module(s) 7 connects to the electronic tongue board 50, to which two or more electronic tongue modules 7 can be connected in any of the two boards according to the needs of the user.

FIGS. 4, 4A and FIG. 4B specify the functions and parts of the main boards. Thus, firstly, there is the processing board 16, which by its connector 1.3 is responsible of acquiring the data sent by the electronic nose board via the connector 51.1 and the electronic tongue connector 50.1, to the processing board connector 16.2, the data are sent to the computer via USB connection 16.5. This board 16 will perform the pre-processing of the data coming from the nose board 51 and the tongue board 50, as well as it also provides energy to the two boards 50 and 51.

In addition, the processing board 16 has another very important function, since it is responsible of controlling the direct current (DC) programmable power source, given that through the connector 16.4 the voltage and amperes can be controlled according to a previous programming which is made in the computer software of the computer 1. The electronic nose-tongue device can be directly connected to the water inlet piping in the electro-coagulation treatment plants, and the water contamination can be analyzed in real time, since the computer software is capable of determining the amount of energy that must be used in the power source in the electro-coagulation process according to the degree of contamination of the water.

The electronic nose board 51 receives the data sent by the hub boards 15 which are also connected to the sensing boards 6. The cables of the hub boards 15 and the pumps 8, 9 pass over the internal part of the main support 10 and are connected to the nose board 51.2, wherein by such connection the power to the pumps 8, 9 and the heaters 14 is also sent.

The functions of the portable computer 1 are as follow: the computer software runs in said portable computer 1, wherein the software directly handles the processing board 16. Thus, from the computer 1 through the software can turn on or off the system, the suction and expulsion pumps cycles can be configured, also the system is trained with the software, whereby the user can teach the electronic nose-tongue device to detect different substances whether these are gases or liquids according to the specification required by the user. The algorithm will run in the computer software, the computer 1 shows in the display the concentration of specific gases, and in case of contamination in the water, it determines the substance and the possible concentration thereof, thus the system can be configured to determine when the concentration in the environment or water is dangerous in order to activate the visual alarm. In this regard, the portable computer 1 also has a display, preferable a touch-screen, which allows the user to manipulate the software in the computer 1.

Thus, the electronic nose boards 50 are connected via the connector 50.1 to the connector 16.3 of the processing board, wherein these boards generate the electric pulses so the electronic tongues 7 can create the reaction and carry out the measurement and analysis process.

Now, FIGS. 5, 5A, 5B, 5C and 5D illustrate and show in detail the electronic nose module with its sensors matrix, as well as the suction 8, and gas expulsion 9 pumps and the valve 6.

In this sense, the electronic nose is composed by a maximum of 10 to 40 sensors 5, including temperature, relative humidity, gamma radiation, beta, and X ray sensors, and from 10 to 30 gas sensors, wherein each sensor allows different type of gases to be detected, and the configuration thereof can be made by the user according to the needs.

In this regard, each sensor 5.1 can be assembled in the sensing module 5. The sensor board is composed by a connector 5.2 which connects to the hub boards 15.2, wherein it can perform the data transfer and receive the power supply, by the electronic nose board 51.

The suction pump 9 is assembled in the chassis 4 and is connected to the electronic nose board 51 where the power 9.3 is provided. Thus, the suction pump 9 is responsible of suctioning the outer air by means of the orifices 9.1 and to send it into the chassis 9.2 where the sensors are located. In this regard, when the air enters the chassis 4, the sensors detect if said air has dangerous concentrations of gases, and if so, the sensor generates a curve 510 as referred to in FIG. 5B according to the degree of concentration of the sample. Thus, the greater the curve 510 the longer the input air cycle by means of the suction pump 9 configured by the user 500, after this time the gas expulsion pump 8 is driven, extracting thereby the air or gases inside the chassis, which is performed through the orifice located in the upper part of the pump 8.2. The expulsion of gases corning from the chassis 4 to the environment is performed by means of the expulsion orifices 8.1.

This process helps to stabilize the signal generated by the sensors and to avoid its saturation 600. Thus, the curves generated by each sensor 510 are unique fingerprints which form a unique pattern of the analyzed gas or substance. The gas expulsion pump 8 has the same configuration as the gas suction pump 9. The gas expulsion pump 8 is assembled directly in the chassis 4 and is connected to the nose board 51 where the power supply 8.2 is received. The pumps cycles and rates can be configured from the software in the portable computer 1.

FIG. 5D illustrates how the sensors boards work. There are different types of boards, including the hub boards 15 which are responsible of transferring data and power to the sensors and heaters. These boards have one data transfer connector 15.2 per each three sensors. There is a total of 6 to 10 hub boards 15 connected to the sensors, wherein a hub board is connected to the resilient heaters 14. Each hub board is connected to the nose board 51 and is located inside the chassis 4 as shown in FIG. 5.

Figure 6:
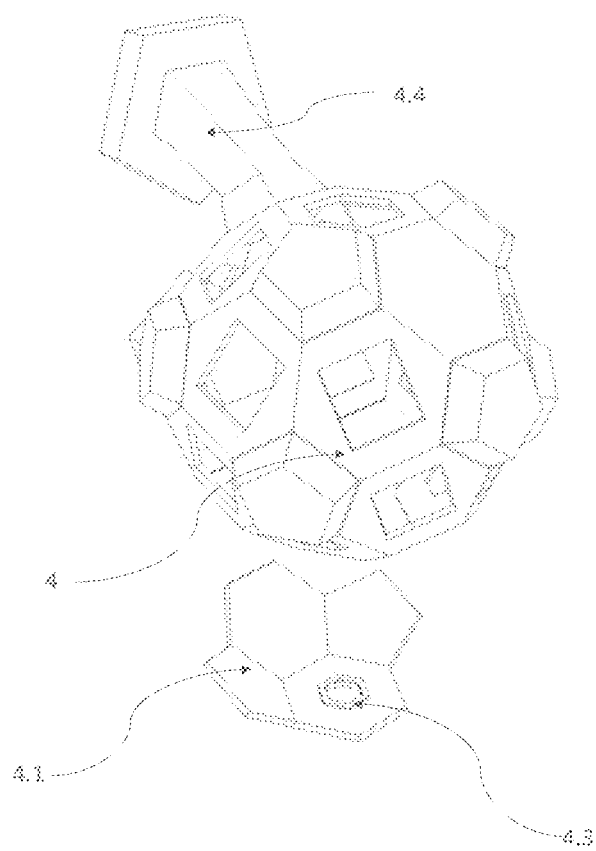
FIG. 6 corresponds to a general view of the chassis of the device of the present invention and its assembly.
Figure 7D:
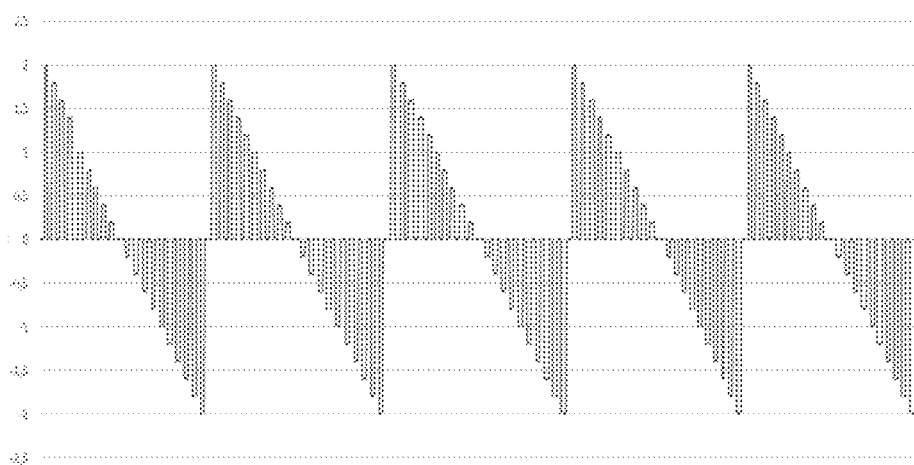
FIG. 7D corresponds to a graph showing the 2 volt stimulus signal coming out of the board in the electronic tongue.

FIGS. 6, 6A and 6B illustrate and explain the way the different pieces are assembled in the chassis 4. In the upper part of the chassis 4 we can find the main support 10, through which the cables of the hub boards and the pumps are passed connecting with the electronic nose board and supporting the board box 2. In the front part of the chassis 4, the computer fastener 10.1 is assembled, which function is to support the computer 1. The chassis 4 also can be installed or located in walls or structures 4.4 allowing it to be anchored in different places and to be fixed. In the lower part, we can find the pumps 8, 9 as well as the chassis cover 4.1, wherein the chassis cover 4.1 is assembled to the valve 6, which allows the entrance of gases to the electronic nose module.

As may be appreciated, the structural design of the nose module is very unique. In particular, in a preferred embodiment, the nose module may be designed as a modular geodesic sphere. In an even more preferred embodiment, the nose module may be designed as a modular truncated icosahedron with 20 hexagonal faces and 12 regular pentagonal faces.

As may be seen in FIG. 6, the structural frame of the nose module or chassis 4 may comprise a plurality of openings. In particular, the openings may be located on the hexagonal faces. In the embodiment shown in FIG. 6, thee openings are square in shape but the openings may be any shape. Preferably, the openings fit within the flat face of the hexagonal face. Each one of the openings may be an interface for a modular sensor or other modular device. This is beneficial because it provides a flat mounting surface for each modular device while at the same time creating an enclosed chamber on the interior of the chassis 4 or structural frame of the geodesic dome. Of course, the enclosed chamber is only created when the openings are filled with modules or cover plates, Cover plates may be used to cover the openings when a sensor module or other modular device is not installed.

In the embodiment shown in FIG. 6, almost all of the hexagonal faces include an opening and can receive a modular sensor or other device and all of the pentagonal faces are fixed faces with no opening. In preferred embodiments, the pentagonal faces are fixed and used as hub boards to help facilitate wiring as shown in FIG. 5D. However, in other embodiments, some or all of the pentagonal faces may also have openings to receive modular sensors. In some embodiments, the pentagonal faces may have openings and receive the hub boards as modular inserts.

As may be appreciated from FIG. 6, an enclosed chamber on an interior of the structural frame is not formed until all the openings are filled. In a preferred embodiment, at least one of the structural faces, and preferably a hexagonal face in the bottom of the nose module, includes an intake port 4.3 to allow gas to enter the enclosed chamber.

Although any number of openings may be filled with modules that are sensor modules, in a preferred embodiment, a plurality of the modules are sensor modules arranged to sense the gas in the interior of the enclosed chamber. Also in a preferred embodiment, at least one of the openings includes an intake pump and at least one of the openings includes an output pump. These may be seen as 8 and 9 respectively in FIG. 5C.

FIGS. 7, 7A, 7B, 7C and 7D illustrate and focus in showing the electronic tongue module 7, which is used to perform the measurement of different liquids. Said electronic tongue module 7 works with the electro analytic principle of pulse amplitude voltametry, wherein the electronic tongue module is composed by working electrodes 7.2, wherein such electrodes 7.2 are connected to the electrode head 7.6, which besides of containing the electrodes 7.2, provides the power allowing thereby the generation of electric pulses which go to the pulse generating boards 50, as shown in FIG. 8D, which allows an oxidation and reduction reaction in the liquid being analyzed which will be recorded by the reference electrode 7.3. The working electrodes 7.2 are composed by different metals with different electro-negative properties, among which can be used precious metals such as gold, platinum, rhodium, iridium or non-precious metals such as zinc, lead, copper, cobalt and graphite.

FIG. 7C shoes the shape of the pulse 700 as a response to what is generated by the redox (reduction-oxidation) type reaction by each metal, each fingerprint is unique which summing up the total of fingerprints from the five electrodes

7.2 gives as a result, a unique fingerprint, wherein this fingerprint will be analyzed by the software in the computer 1 with the algorithm.

FIGS. 8, 8A, 8B and 8C, illustrate how the nose-tongue device of the present invention is coupled to the support structure in any piping where different types of liquids are required to be analyzed or monitored, and to determine the functioning of the programmable power source controlled by the software in the computer 1.

Thus, the support structure 800 allows to hold or support and to connect the nose module and the tongue module in different pipes, whether it is outdoor or in places with controlled environment. The structure 800 includes incorporated therein a suction pump 605 with greater power, wherein such pump 605 suctions the liquid passing by the pipe 606 and sends it to the sample containers 600, 603 for a further analysis by the electronic nose and tongues.

Here, in this connection mode with the water piping the pumps cycle is changed, whereby the suction pump 9 will perform the suction and expulsion of gases, during time intervals configured by the user, while the gas expulsion pump 8 now will generate an air stream so as to be able to generate bubbles in the liquids inside the sample containers 600. The change of cycle and the functioning time of the pumps are performed and controlled by the software in the computer 1. In the electronic tongue module 7 the respective measurements are also made, wherein these will connect to the sample containers 603, whereby the tongue modules must be submerged in the liquid to be analyzed.

After the information sent by each of the nose and tongue modules is analyzed, the software in the computer 1 determines how much energy must be applied by the programmable DC power source 200, while the main power source will be connected to the power source connectors 16.1 which are in the processing board 16. The power source adjusts its voltage and amperes according to the previous programming provided and configured in the software of the computer 1. These sources existing in the market can manipulate several power sources (saves) which allow several electrical devices to be controlled by giving instructions to only one of them.

The programmable power source 200 can manipulate several devices such as electrovalves, alarms, pumps, water sprayers, gas extractors, but its main function is featured in the electro-coagulation water treatment systems. This system works by letting electricity to pass through aluminum and steel electrodes allowing thereby the contaminant particles in the water to be caught with the floccules produced in the positive electrode provided in the electrochemical reaction.

The device of the present invention can determine the amount of energy that must be used in the electro-coagulation according to the sensed contamination level, which represents a greater efficiency in the process since the cost of energy and maintenance is reduced.

Figure 8C:
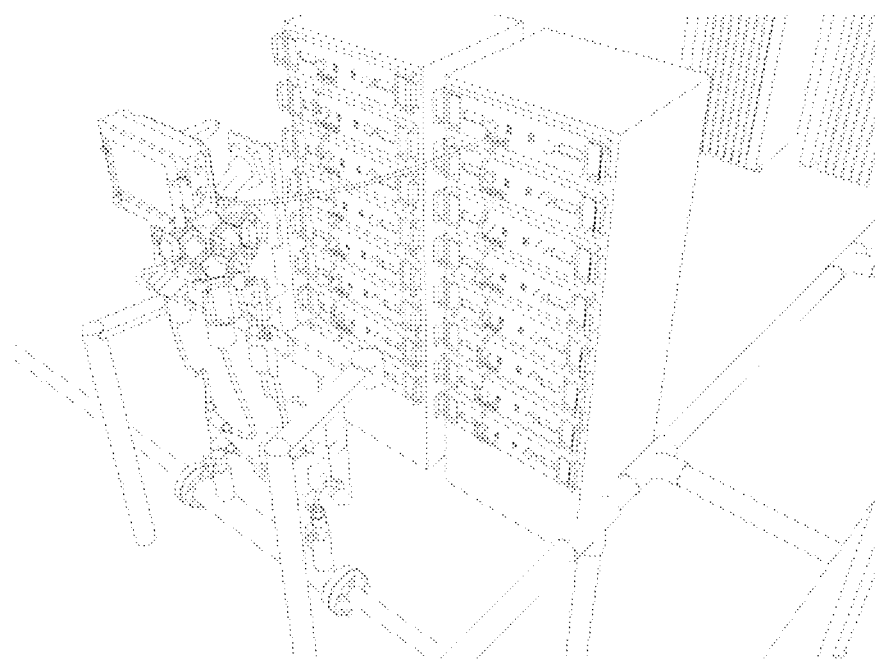
FIG. 8C corresponds to a side perspective view of the device of the invention in functioning.

FIGS. 8B and 8C illustrate the way how the device of the present invention works in a treatment plant, controlling several power sources connected to different electro-coagulators.

Figure 9:
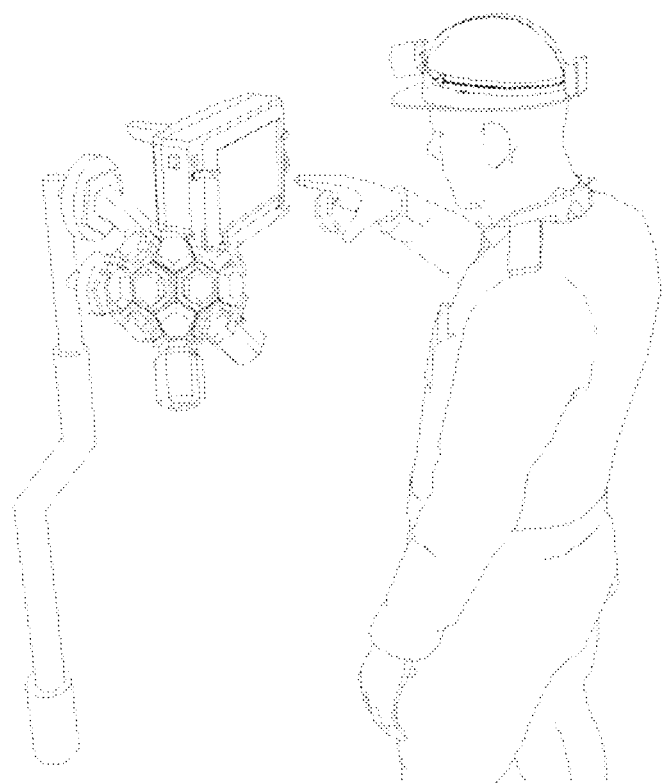
FIG. 9 corresponds to a genera; view of the device functioning only with the electronic nose module being configured by the user.
Figure 9A:
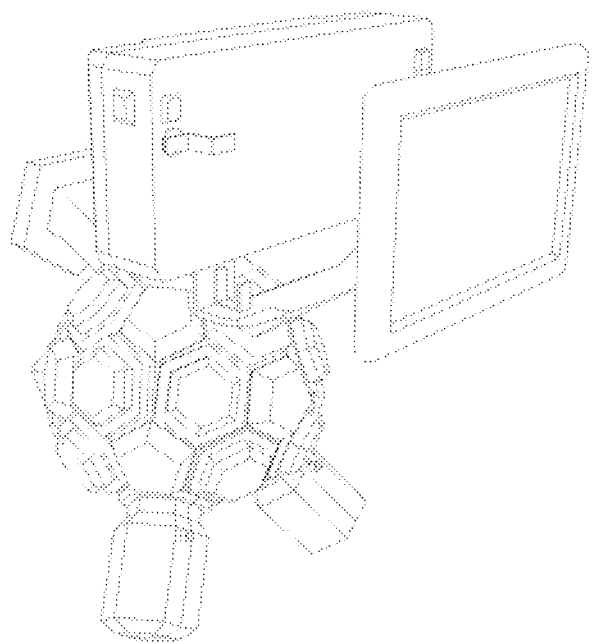
FIG. 9A corresponds to a detailed view of the device of the invention having only the electronic nose module.

FIGS. 9 and 9A illustrate the configuration wherein only the electronic nose is used, wherein this kind of configuration is suitable and useful to be able to detect leaks of toxic, flammable, choking and radioactive gases, wherein this kind of substances are very common in places where gas, oil, chemicals, or highly dangerous substances are stored, which can be found in different industries such as the extraction of oil by hydraulic fracking where radioactivity can be found coming from the wellbore where small sources of uranium can be found.

In FIGS. 9 and 9A, it can be seen the configuration of the nose to detect these substances in the environment. This kind of electronic nose can be installed in different structures which are in places with great potential of leaks, wherein it can also be seen the operator watching the result of the analysis in real time, at the same time that he/she can perform the configuration of the device according to the needs of the place.

In an embodiment of the invention, the device of the present invention can be controlled remotely, wherein this process can be carried out through a connection module, such as a modem connecting to the computer 1, allowing updates in the algorithm or corrections in the system to be performed without the need of having onsite personnel.

In an alternative embodiment, the device of the present invention can be portable, that is, it can be carried by an operator and will not require a support structure making it stationary, in order to be able to be carried to remote areas and to be connected in a simple and quick manner.

Now, the device of the present invention allows an electronic nose function at the same time that it can perform an electronic tongue function, wherein these two functions are defined below for explanation purposes only and do not intend to limit the scope of the invention.

Electronic Nose Function

The electronic nose is composed by some air pumps which absorb the air around so as to send it afterwards to the electronic nose which is composed by a capsule of gas sensors.

The nose sensors interpret the information in the form of signals, which are represented as a curve.

Then, the curved signals then are analyzed by specific computer software, which has an algorithm that allows to classify the information and to teach the system to distinguish different substances.

Then, all this information is pre-processed by the processing board and after that is processed by the computer with the algorithm which will allow to sense hundreds of gases in real time, displaying the necessary information.

Finally, the computer determines through the computer software whether the gases or liquids analyzed are dangerous or not, if it is determined that the concentrations are dangerous according to a previous learning, a visual alarm will be issued.

Electronic Tongue Function

The electronic tongue works with the principle of reduction and oxidation within the volt metric technique, i.e. it works with working electrodes and reference electrode, wherein the working electrodes are responsible of generating electric pulses, these pulses generate a specific signal in the liquid being analyzed, and these signals are captured by the reference electrode.

The pulse shapes are unique for each reference electrode receiving the same for each working electrode, afterwards the computer software sorts the information and teaches the system to distinguish these different substances.

Then, all this information is pre-processed by the main hardware, after that the information is sent to the computer for processing in the artificial intelligence algorithm having the computer software.

Finally, the portable computer through the software determines whether the liquids analyzed are dangerous or not, and depending if the concentration of substances is determined to be dangerous, the visual and vibratory alarm will be issued.

Function in Electronic Nose-Tongue in Monitoring Water

The electronic nose-tongue connects to the treatment plant water inlet piping, allowing to take the measurements with the nose and tongue. It will also be connected to a programmable direct current (DC) power source.

The monitoring is performed in real time through the use of the computer program with the artificial intelligence algorithm which will allow the information to be sorted.

After the sorting, the water contamination degree will be determined and according to a previous learning it establishes the amount of energy to be used by the programmable source code in the electro-coagulation treatment plant.

Software

As explained above, the system including the tongue sensor and nose sensor maybe run by custom software. The custom software may provide many benefit including a graphical user interface to allow operation and control of the system. In addition to providing an interlace, the software may analyze the data being received from the various sensors of the system.

In a preferred embodiment, artificial intelligence algorithms are used to analyze the data being received from the sensors. The artificial intelligence algorithms may be capable of classifying and training the system so as to recognize the different sign patterns sent by the electronic nose and the electronic tongue. In preferred embodiments, known quantities of contaminants are provided to and analyzed by the system to allow the systems artificial intelligence algorithms to learn the sensor responses for particular contaminants. Once the system has learned what a contaminant response locks like from the sensors, the system can then detect the contaminant in a real world sample based on the responses it has learned from the known contaminants.

Numerous different types of artificial intelligence algorithms can be used. For example, regression may be used. Regression algorithms may include but are not limited to Ordinary Least Squares Regression (OLSR), Linear Regression, Logistic Regression, Stepwise Regression, Multivariate Adaptive Regression Splines (MARS), and Locally Estimated Scatterplot Smoothing (LOESS).

In other embodiments, instance based artificial intelligence algorithms may be used. Instance based algorithms may include but are not limited to k-Nearest Neighbour (kNN), Learning Vector Quantization (LVQ), Self-Organizing Map (SOM), and Locally Weighted Learning (LWL).

Regularized algorithms may also be used. Regularized algorithms include but are not limited to Ridge Regression, Least Absolute Shrinkage and Selection Operator (LASSO), Elastic Net and Least-Angle Regression (LARS).

In yet other embodiments, other types of artificial algorithms may be used including Decision Tree algorithms. Decision tree algorithms include but are not limited to Classification and Regression Tree (CART), Iterative Dichotomiser 3 (ID3), C4.5 and C5.0 (different versions of a powerful approach), Chi-squared Automatic Interaction Detection (CHAIR), Decision Stump, M5 and Conditional Decision Trees. In still yet other embodiments, other types of artificial intelligence may be used including Bayesian algorithms, clustering algorithms, associated rule learning algorithms, Artificial Neural Network Algorithms, deep learning algorithms, Dimensionality Reduction Algorithms, and Ensemble Algorithms.

In preferred embodiments, regardless of which artificial intelligence algorithms are used, the system is "taught" all the different possible contaminants it needs to detect through the learning process of providing known samples to analyze. The system may then be placed in use and can detect the inclusion of the contaminants in new samples by comparing the response of the sensors to the new samples against the known samples using the artificial intelligence algorithms.

The classification process with the electronic nose and tongue has its central part in the preprocessing of the raw data obtained directly from the hardware. Once pre-processing of the data is completed, descriptors are sent to an artificial intelligence algorithm which is able to learn from a training set and then to put a label to a new, unknown, sample. This system is currently using the algorithm of support vector machines (SVM); however, as mentioned previously, the basis of our algorithm is in the preprocessing and not in the classification itself The preprocessing includes a step of filtering each of the sensor signals. It continues with an analysis of the signal-to-noise ratio that defines how noisy each of the sensor signals is. Subsequently our algorithm defines from what ratio it is considered a signal as valid, or not noisy. Then are selected just the best sensors. Selected sensors are those for which more than certain percentage of the training samples are not noisy. Features are extracted only for the selected sensors. This process is done primarily because depending on the domain in which the tongue and nose are applied, some sensors can behave better than others. After selecting the sensors, each signal features are extracted to send them to the trainer (in training process) and the classifier (in classifying process), which is done for each read cycle. The algorithm only analyses data from cycles that are not on the border (neither the first cycle, neither the last one) to prevent the inertia of the system that may cause bad features. Features are associated with rise time, fall time and amplitude of the signal at different moments.

In addition to doing the primary task of analysis, the software may provide a graphical user interface ("GUI") to allow the user to interface and operate the sensor system. The graphical user interface may provide all the typical features like login screens, data entry and mode selection screens.

Figure 10:
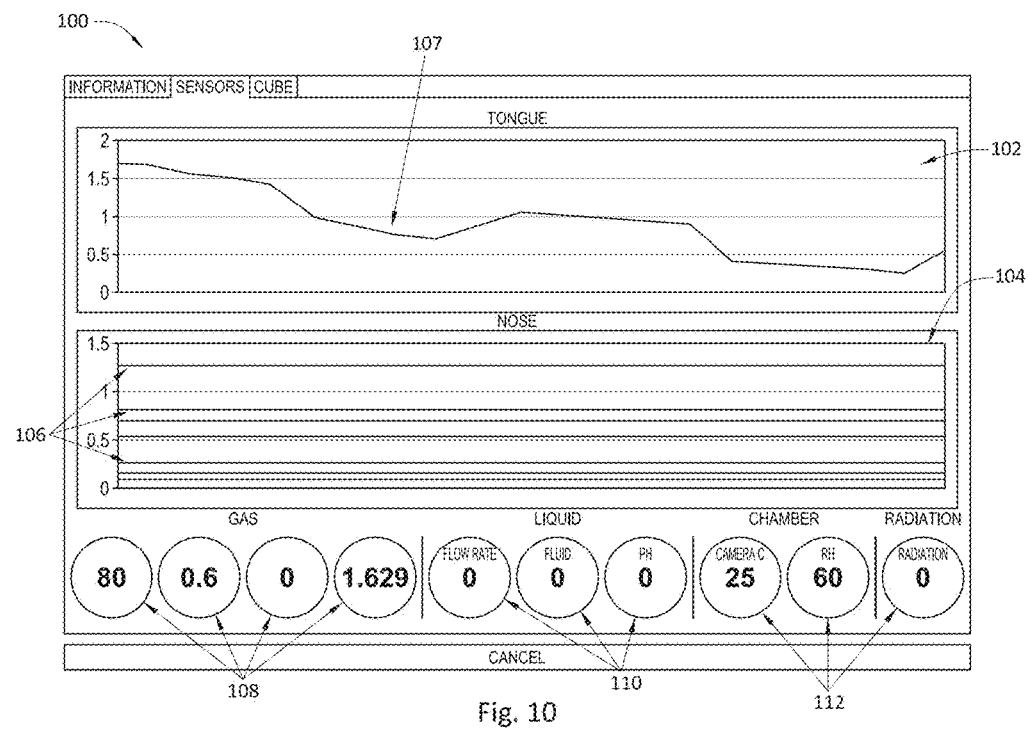
FIG. 10 illustrates a screen of a graphical user interface that displays the output of the tongue module and nose module in real time.

In some embodiments, the GUI can display the results of both the nose sensor and one or more tongue sensors on the screen in real time. FIG. 10 illustrates a screen 100 of a graphical user interface that displays the output of the tongue module and nose module in real time. In operation, the monitoring system can receive input from one or more sensors in the nose module and display the results on a two-dimensional graph 104 as continues lines 106 where the scale of the x-axis and the continuous lines are constantly updated to accommodate new input from the nose module. In addition, the monitoring system can receive inputs from one or more tongue modules and simultaneously displaying the results of each of a plurality of electrodes in a two-dimensional graph 102 as a continuous line where the scale of the x-axis and the continuous line are constantly updated to accommodate new input from the tongue module.

In addition to two-dimensional graphs 102 and 104, the screen may include other data output. For example, the numerical outputs 108 of each sensor may be displayed. The software may allow the user to set alarm limits and if the output of a particular sensor exceeds the alarm limit, the numerical output 108 may be turned red to indicate an alarm is being violated. The software may be set such that if an alarm is ever exceeded the display of the output stays red or it may switch back to a different color if the output comes back below the alarm levels.

In preferred outputs, the numerical outputs may be displayed as percent/volume of a particular contaminant. These percent/volumes may be calculated based on the artificial intelligence algorithms. In addition to the gas level outputs 108, the screen 100 may also show liquid numerical outputs 110. Similar to the gas outputs 108, the liquid numerical outputs 110 may be updated in real time. In some embodiments, the liquid numerical outputs 110 may include flow rate, liquid, PH. In other embodiments, other outputs may be used.

In preferred embodiments, the numerical outputs 108 and 110 can be user selected. To this end, the user can configure the software to output any numerical output desired based on the area available on the screen 100.

In some embodiments, the system may be configured to also detect radiation by including a radiation sensor as part of the nose module. In such embodiments, the numerical values of the radiation sensor may be displayed as radiation numerical output 112.

Figure 11:
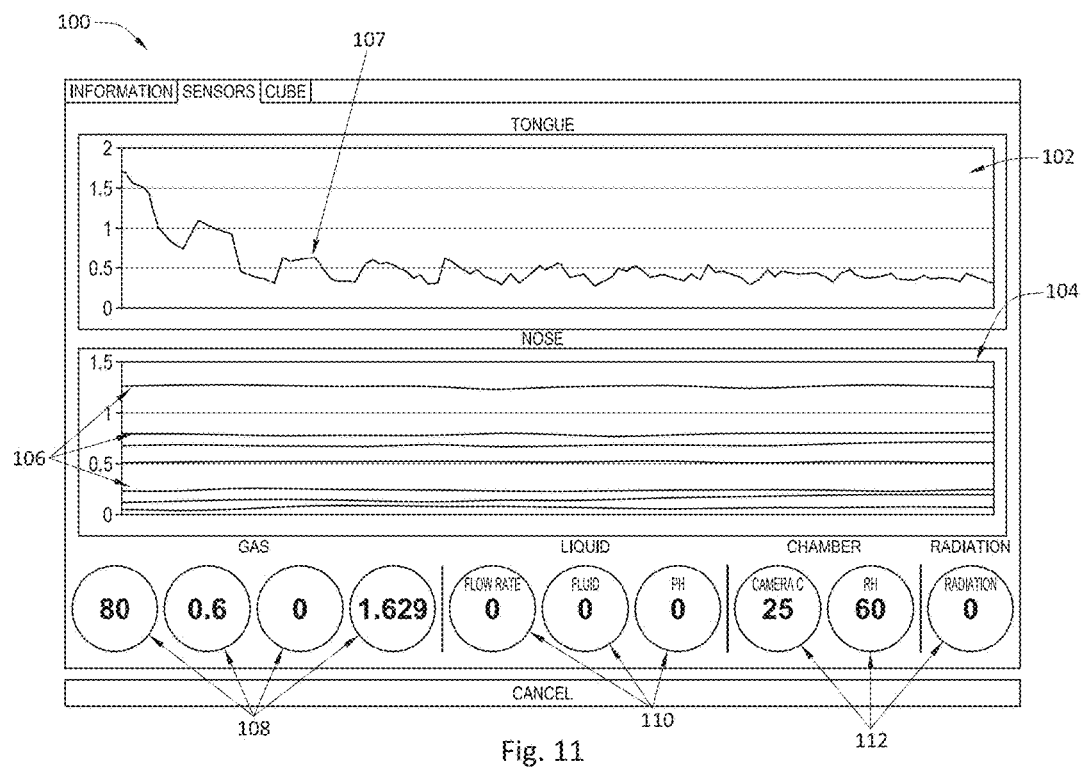
FIG. 11 illustrates the screen of FIG. 10 a short while later.

FIG. 11 illustrates the screen of FIG. 10 a short while later. As may be seen in FIG. 11, the graphs 102 and 104 along with the lines 106 and 107 representing the outputs of the nose and tongue modules, are dynamically updated in real time. In particular, the scale of the x-axis of the graphs 102 and 104 is dynamically changed to compensate for more and more data being output by the nose and tongue modules. In particular, the scale of the x-axis may be increased. However, this attribute may also be user configurable and the user may set the scale to be fixed to a specific scale. In some embodiments, the x-axis scale may continuously update until a certain scale is reached and then remain fixed.

Figure 12:
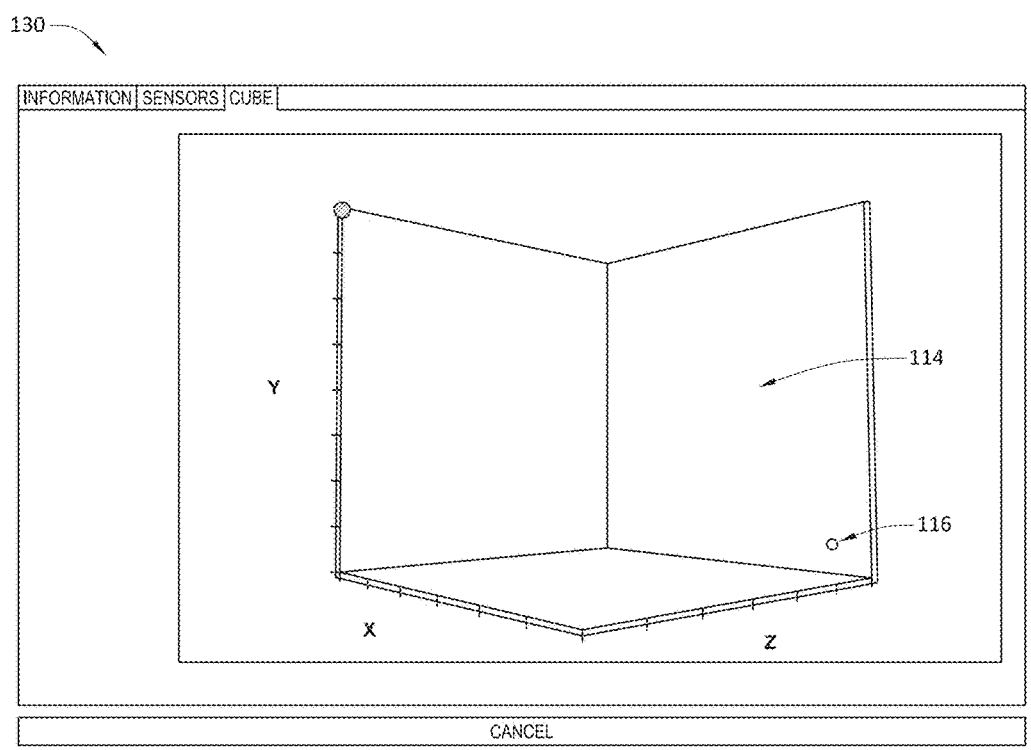
FIG. 12 illustrates a graphical user interface of a three-dimensional graph with a substance point.

In addition to displaying data from the nose and tongue modules in real time on screen 100, the software may include screens to show the substances detected and allow users to define limits for when those substances are present. FIG. 12 illustrates a graphical user interface 130 of a three-dimensional graph 114 with a substance point 116. The various axis of the graph define the lineal transformations of all the values displayed by the sensors, depending on the scenario, the distance between a new point and the reference point can have a physical value like the concentration of certain chemical compound. As may be seen in FIG. 12, a substance point 116 is defined by its location within the three axis. As will be explained below, the substance point may be defined within a substance cube.

Figure 13:
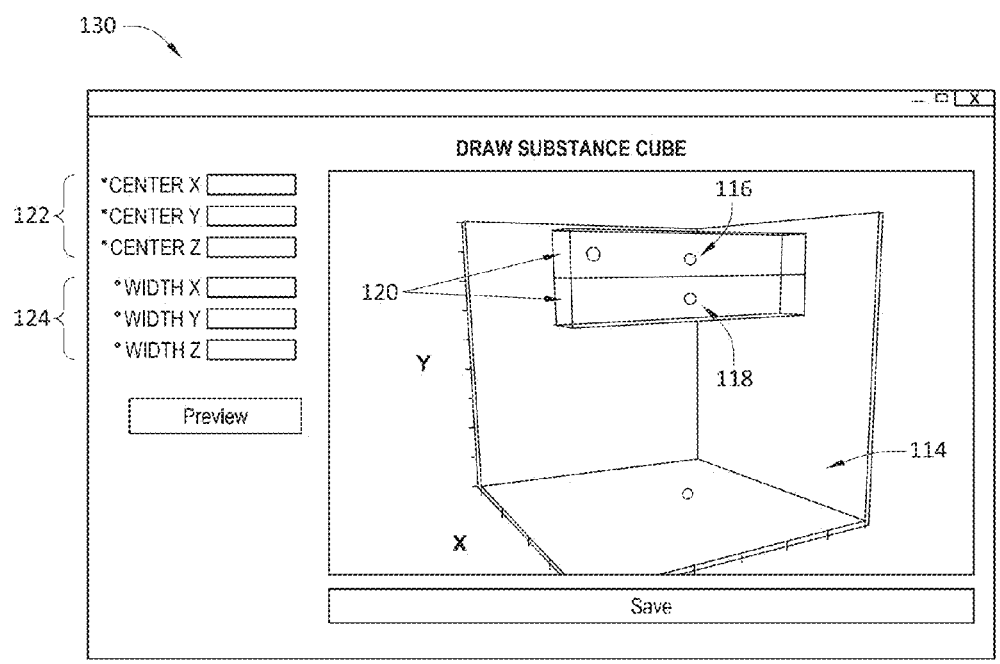
FIG. 13 illustrates a graphical user interface for defining and observing a substance cube.

FIG. 13 illustrates a graphical user interface 130 for defining and observing a substance cube 120. To make the software easier to handle, a friendly graphic interface 130 may be used to define parameters through the use of a substance cube 120. This interface 130 creates a method for inputting parameters to define when a substance has been detected. The software displays a three-dimensional graph 114 on a screen where each axis of the three-dimensional graph 114 represents a particular parameter for detecting the substance in question. A rectangular volume, also known as a substance cube, 120 can be defined in the three-dimensional graph 114 and can be displayed. The limits of the rectangular volume 120 can be used to establish parameters defining when a substance has been detected. A substance is then analyzed by the system and a point 116 is displayed on the three-dimensional graph 114 that represents the output of the sensors in terms of the axis of the three-dimensional graph 114. Finally, if the point 116 is within the limits of the rectangular volume 120 to determine whether the substance has been detected. If the point 116 falls within the volume of the defined rectangle 120, then the substance is present.

Each substance may have a unique cube 120 in a three-dimensional graph 114. Every time an identification is made a point 116 in that three-dimensional axis 114 is generated. If the point 116 falls within the cube 120, it means that the substance being analyzed is the substance previously learned by the system. The dimensions of the substance cube 120 may be determined by the algorithm taking into account several characteristics of the substance patterns.

In preferred embodiments, the analyzing step is performed by a nose module and a tongue module and data from both modules is analyzed by a single processor. In some embodiments, the displaying steps occur on a touch screen that allows the rotation of the three-dimensional graph 114. Although the size and shape of the substance cube 120 may be defined by the algorithms of the software, in some embodiments, the substance cube 120 is defined by entering a center point 118 and widths for the rectangular volume in each axis of the three-dimensional graph. To this end, the display may allow inputs 122 for a substance cube center point 118 and inputs 124 for a substance cube width.

Although the inventions have been described with reference to preferred embodiments and specific examples, it will readily be appreciated by those skilled in the art that many modifications and adaptations of the methods and devices described herein are possible without departure from the spirit and scope of the inventions as claimed hereinafter. Thus, it is to be clearly understood that this description is made only by way of example and not as a limitation on the scope of the embodiments as claimed hereafter.

What is claimed is:

1. A real-time, in-situ monitoring and analyzing device of liquid or gaseous substances, comprising:
   an armored electronic circuit box;
   a computer located in a front outer part of the armored electronic circuit box, and the computer connected to a data processing and acquisition electronic circuit contained in the armored electronic circuit box;
   electronic tongue electronic circuits and an electronic nose electronic circuit within the armored electronic circuit box and connected to the data processing and acquisition electronic circuit;
   luminous alert devices located on an outside of the armored electronic circuit box;
   an electronic nose connected to the electronic nose electronic circuit and to sensors of sensing modules; said electronic nose formed by:
      a convex polyhedral shaped capsule with pentagon and hexagon faces, wherein the following elements are disposed: sensing modules, hub electronic circuits, a valve, a gas expulsion pump and a gas suction pump, all of which being assembled in perforations in the faces of the convex polyhedral shaped capsule; and
      heating resistances disposed in an inner chamber of the convex polyhedral shaped capsule in front of the sensing modules; and
   electronic tongues each connected to a tongue electronic circuit and to the sensors of the sensing modules; said electronic tongues being formed by:
      working electrodes connected to an electrode head; and
      a reference electrode concentric relative to the electrode head.

2. The device of claim 1, wherein the device further comprises a main support inside of which pass connection cables for the sensors, the gas expulsion pump and the gas suction pump, and the main support is assembled between an upper part of the convex polyhedral shaped capsule and a back part of the armored electronic circuit box; the convex polyhedral shaped capsule also having a cover.

3. The device of claim 1, wherein the electronic nose is composed of 10 to 40 sensors selected from the group consisting of temperature sensors, relative humidity sensors, gamma radiation sensors, beta radiation sensors, X ray radiation sensors, and of 10 to 30 gas sensors.

4. The device of claim 1, wherein the gas suction pump comprises suction orifices and a capsule gas extraction orifice.

5. The device of claim 1, wherein the gas expulsion pump comprises an orifice for gas expulsion inside the convex polyhedral shaped capsule, located in an upper part of the pump, and gas expulsion orifices.

6. The device of claim 1, wherein the device has one hub electronic circuit per each three sensors and has a total of 6 to 10 hub electronic circuits connected to the heating resistances, and wherein each hub electronic circuit is connected to the electronic nose electronic circuit and are located inside the convex polyhedral shaped capsule.

7. The device of claim 1, wherein the convex polyhedral shaped capsule further comprises in its front part a computer fastener, and wherein said convex polyhedral shaped capsule can be installed in walls or fixed surfaces.

8. The device of claim 1, wherein the working electrodes of the electronic tongues are composed of metals selected from the group consisting of gold, platinum, silver, titanium, rhodium and iridium, or non-precious materials selected from the group consisting of zinc, lead, copper, cobalt and graphite.

9. The device of claim 1, wherein the device is further connected to a sample suction tube, which is also linked to a suction pump, and said suction pump is connected to sample containers in contact with the electronic tongues and the electronic nose.

10. The device of claim 9, wherein the sample containers are also connected to a sample return tube.

11. The device of claim 9 or 10, wherein the device along with the sample containers and the suction pump are supported by a support structure.

12. The device of claim 1, wherein the device is portable and further comprises a remote control connection module wherein the remote control connection module is a modem connected to a computer.

13. The device of claim 1, wherein the device is portable and is connected to one or more DC programmable power sources linked to the data processing and acquisition electronic circuit through power source connectors and a connector; and the device is also connected to a tube for input of polluted water in a water treatment plant formed by electro-coagulators, wherein said device is configured to analyze the pollution of water in real time and to determine an amount of energy that must be sent by the DC programmable power source(s) according to a degree of contamination of the polluted water sensed by the electronic nose and the electronic tongues.

* * * * *